(12) United States Patent
Broering et al.

(10) Patent No.: US 7,270,861 B2
(45) Date of Patent: Sep. 18, 2007

(54) LAMINATED STRUCTURALLY ELASTIC-LIKE FILM WEB SUBSTRATE

(75) Inventors: Shaun Thomas Broering, Ft. Thomas, KY (US); Daniel Charles Peck, Cincinnati, OH (US); John Joseph Curro, Cincinnati, OH (US); Robert Haines Turner, Cincinnati, OH (US); Jody Lynn Hoying, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 221 days.

(21) Appl. No.: 10/980,219

(22) Filed: Nov. 3, 2004

(65) Prior Publication Data

US 2005/0123726 A1    Jun. 9, 2005

Related U.S. Application Data

(63) Continuation-in-part of application No. 10/737,430, filed on Dec. 16, 2003, which is a continuation-in-part of application No. 10/610,299, filed on Jun. 30, 2003, now abandoned, which is a continuation-in-part of application No. 10/324,661, filed on Dec. 20, 2002, now abandoned.

(51) Int. Cl.
*B32B 1/08* (2006.01)
*B32B 3/10* (2006.01)
*B29D 23/00* (2006.01)

(52) U.S. Cl. .................. 428/35.7; 428/36.9; 428/36.91; 428/133; 428/139; 428/172

(58) Field of Classification Search ........ 428/131–134, 428/136–139, 156, 167, 172, 35.7, 36.9, 428/36.91
See application file for complete search history.

(56) References Cited

U.S. PATENT DOCUMENTS

| | | |
|---|---|---|
| 2,068,456 A | 1/1937 | Hooper |
| 2,275,425 A | 3/1942 | Grabec |
| 2,404,758 A | 7/1946 | Teague et al. |
| 2,633,441 A | 3/1953 | Buttress |
| 2,748,863 A | 6/1956 | Benton |
| 2,924,863 A | 2/1960 | Chavannes |

(Continued)

FOREIGN PATENT DOCUMENTS

EP    0 509 012 B1    7/1995

(Continued)

OTHER PUBLICATIONS

U.S. Appl. No. 11/156,020, filed Jun. 21, 2005, Hammons et al.

*Primary Examiner*—Jenna-Leigh Befumo
(74) *Attorney, Agent, or Firm*—David K. Mattheis; Peter D. Meyer; Leonard W. Lewis

(57) ABSTRACT

The present invention relates to film web substrates and more particularly to such web substrates wherein the inherent elongation properties of a given web material are modified. An exemplary web material is formed from first and second precursor webs. A first side of the web material is formed from the first precursor web and integral extensions of the second precursor web that extend through the first precursor web.

9 Claims, 5 Drawing Sheets

U.S. PATENT DOCUMENTS

| | | |
|---|---|---|
| 3,073,304 A | 1/1963 | Schaar |
| 3,081,500 A | 3/1963 | Griswold et al. |
| 3,081,512 A | 3/1963 | Griswold |
| 3,137,893 A | 6/1964 | Gelpke |
| 3,355,974 A | 12/1967 | Carmichael |
| 3,511,740 A | 5/1970 | Sanders |
| 3,542,634 A | 11/1970 | Such et al. |
| 3,566,726 A | 3/1971 | Politis |
| 3,681,182 A | 8/1972 | Kalwaites |
| 3,681,183 A | 8/1972 | Kalwaites |
| 3,695,270 A | 10/1972 | Dostal |
| 3,718,059 A | 2/1973 | Clayton |
| 3,760,671 A | 9/1973 | Jenkins |
| 3,881,987 A | 5/1975 | Benz |
| 3,949,127 A | 4/1976 | Ostermeier et al. |
| 3,965,906 A | 6/1976 | Karami |
| 4,035,881 A | 7/1977 | Zocher |
| 4,042,453 A | 8/1977 | Conway |
| 4,135,021 A | 1/1979 | Patchell et al. |
| 4,276,336 A | 6/1981 | Sabee |
| 4,379,799 A | 4/1983 | Holmes |
| 4,397,644 A | 8/1983 | Matthews et al. |
| 4,465,726 A | 8/1984 | Holmes |
| 4,469,734 A | 9/1984 | Minto et al. |
| 4,588,630 A | 5/1986 | Shimalla |
| 4,741,941 A | 5/1988 | Englebert et al. |
| 4,758,297 A | 7/1988 | Calligarich |
| 4,781,962 A | 11/1988 | Zamarripa et al. |
| 4,798,604 A | 1/1989 | Carter |
| 4,820,294 A | 4/1989 | Morris |
| 4,840,829 A | 6/1989 | Suzuki et al. |
| 4,859,519 A | 8/1989 | Cabe, Jr. et al. |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer |
| 5,084,324 A * | 1/1992 | Schirmer ............... 428/139 |
| 5,131,141 A * | 7/1992 | Kawaguchi ............ 29/853 |
| 5,144,730 A | 9/1992 | Dilo |
| 5,165,979 A | 11/1992 | Watkins et al. |
| 5,167,897 A | 12/1992 | Weber et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,382,245 A | 1/1995 | Thompson |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,518,801 A | 5/1996 | Chappell |
| 5,533,991 A | 7/1996 | Kirby et al. |
| 5,554,093 A | 9/1996 | Porchia et al. |
| 5,554,145 A | 9/1996 | Roe |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,747 A | 11/1996 | Dais et al. |
| 5,575,874 A | 11/1996 | Griesbach, III et al. |
| 5,580,418 A | 12/1996 | Alikhan |
| 5,599,420 A | 2/1997 | Yeo et al. |
| 5,626,571 A | 5/1997 | Young et al. |
| 5,628,097 A | 5/1997 | Benson |
| 5,648,142 A | 7/1997 | Phillips |
| 5,656,119 A | 8/1997 | Srinivasan et al. |
| 5,658,639 A | 8/1997 | Curro |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro |
| 5,704,101 A | 1/1998 | Majors et al. |
| 5,709,829 A | 1/1998 | Giacometti |
| 5,714,107 A | 2/1998 | Levy et al. |
| 5,723,087 A | 3/1998 | Chappel et al. |
| 5,743,776 A | 4/1998 | Igaue |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson |
| 5,919,177 A | 7/1999 | Georger et al. |
| 5,925,026 A | 7/1999 | Arteman et al. |
| 5,964,742 A | 10/1999 | McCormack et al. |
| 5,968,029 A | 10/1999 | Chappell |
| 5,986,167 A | 11/1999 | Arteman et al. |
| 5,993,432 A | 11/1999 | Lodge |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,096,016 A | 8/2000 | Tsuji et al. |
| 6,114,263 A | 9/2000 | Benson et al. |
| 6,117,524 A | 9/2000 | Hisanaka et al. |
| 6,129,801 A | 10/2000 | Benson et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| D444,631 S | 7/2001 | Woodbridge et al. |
| 6,264,872 B1 | 7/2001 | Majors et al. |
| 6,287,407 B1 | 9/2001 | Stein et al. |
| 6,383,431 B1 | 5/2002 | Dobrin et al. |
| 6,394,651 B2 | 5/2002 | Jackson |
| 6,394,652 B2 | 5/2002 | Meyer et al. |
| 6,395,122 B1 | 5/2002 | Hisanaka et al. |
| 6,395,211 B1 | 5/2002 | Dettmer et al. |
| 6,410,823 B1 | 6/2002 | Daley et al. |
| 6,420,625 B1 | 7/2002 | Jones et al. |
| 6,423,884 B1 | 7/2002 | Oehmen |
| 6,451,718 B1 | 9/2002 | Yamada et al. |
| 6,452,064 B1 | 9/2002 | Thoren et al. |
| 6,458,447 B1 | 10/2002 | Cabell |
| D466,702 S | 12/2002 | Carlson et al. |
| 6,506,329 B1 | 1/2003 | Curro et al. |
| 6,602,580 B1 * | 8/2003 | Hamilton et al. ........... 428/173 |
| 6,620,485 B1 | 9/2003 | Benson et al. |
| 6,632,504 B1 | 10/2003 | Gillespie et al. |
| D481,872 S | 11/2003 | Hennel et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,794,626 B2 | 9/2004 | Copat et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |
| 6,863,960 B2 | 3/2005 | Curro et al. |
| 6,872,274 B2 | 3/2005 | Kauschke et al. |
| 6,884,494 B1 | 4/2005 | Curro et al. |
| 7,005,558 B1 | 2/2006 | Johansson et al. |
| 7,037,569 B2 | 5/2006 | Curro et al. |
| 2002/0029445 A1 | 3/2002 | Laun et al. |
| 2002/0039867 A1 | 4/2002 | Curro et al. |

| | | |
|---|---|---|
| 2002/0105110 A1 | 8/2002 | Dobrin et al. |
| 2002/0119720 A1 | 8/2002 | Arora et al. |
| 2002/0132544 A1 | 9/2002 | Takagaki |
| 2002/0192268 A1 | 12/2002 | Alwattari et al. |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0191442 A1 | 10/2003 | Bewick-Sonntag |
| 2003/0191443 A1 | 10/2003 | Taylor |
| 2004/0121686 A1 | 6/2004 | Wong et al. |
| 2004/0122396 A1 | 6/2004 | Maldonado et al. |
| 2004/0126531 A1 | 7/2004 | Harvey et al. |
| 2004/0131820 A1 | 7/2004 | Turner et al. |
| 2004/0137200 A1 | 7/2004 | Chhabra et al. |
| 2004/0229008 A1 | 11/2004 | Hoying et al. |
| 2004/0247828 A1* | 12/2004 | Brozenick et al. .......... 428/139 |
| 2004/0265533 A1 | 12/2004 | Hoying et al. |
| 2004/0265534 A1 | 12/2004 | Curro et al. |
| 2005/0064135 A1 | 3/2005 | Turner et al. |
| 2005/0096614 A1 | 5/2005 | Perez et al. |
| 2005/0283129 A1 | 12/2005 | Hammons et al. |
| 2006/0087053 A1 | 4/2006 | O'Donnell et al. |

FOREIGN PATENT DOCUMENTS

| | | |
|---|---|---|
| EP | 0 955 159 A1 | 11/1999 |
| EP | 1 004 412 A1 | 5/2000 |
| WO | WO 01/45616 A1 | 6/2001 |
| WO | WO 01/76523 A2 | 10/2001 |
| WO | WO 02/100632 A1 | 12/2002 |

* cited by examiner

LAMINATED STRUCTURALLY ELASTIC-LIKE FILM WEB SUBSTRATE

CROSS-REFERENCE TO RELATED APPLICATIONS

This application is a continuation-in-part of co-pending U.S. patent application Ser. No. 10/737,430, filed Dec. 16, 2003, which is a continuation-in-part of U.S. patent application Ser. No. 10/610,299, filed Jun. 30, 2003, now abandoned, which is a continuation-in-part of U.S. patent application Ser. No. 10/324,661, filed Dec. 20, 2002, now abandoned.

FIELD OF THE INVENTION

This invention relates to film web substrates and more particularly to such web substrates wherein the inherent elongation properties of a given web material may be modified. Specifically, this invention relates to laminates of such webs treated by mechanical formation in which the resistive force exerted by the web material to an applied elongation force can be modified.

BACKGROUND OF THE INVENTION

Flexible films, particularly those made of comparatively inexpensive polymeric materials, have been widely employed for the protection and preservation and containment of various items and materials. Additionally, web materials having modified properties to provide a desired resistive force to an applied elongation force on the web are generally known. Such web materials are described in U.S. Pat. Nos. 5,518,801; 6,394,651; and 6,394,652.

The term "flexible" is utilized herein to refer to materials that are capable of being flexed or bent especially repeatedly such that they are pliant and yieldable in response to externally applied forces. Accordingly, "flexible" is substantially opposite in meaning to terms "inflexible," "rigid," or "unyielding." Materials and structures that are flexible therefore may be altered in shape and structure to accommodate external forces and to conform to the shape of objects brought into contact with them without losing their integrity. Flexible films of the type commonly available are typically formed from materials having consistent physical properties throughout the film structure, such as stretch, tensile, and/or elongation properties.

Flexible film webs that have deformations formed in them are known. A known method for forming such films is by passing a continuous web between a pair of matched forming rollers to form an intentional pattern of deformations on the film. Illustrative of the state of the art with regard to such continuous webs and film materials having intentional patterns of deformations formed therein are described in U.S. Pat. Nos. 5,554,093; 5,575,747; 5,723,087; and 6,394,652. Accordingly, an object of the present invention is to provide web materials that exhibit differential elastic-like behavior in the direction of applied elongation without the use of added materials. As used herein, the term "elastic-like" describes the behavior of web materials that, when subjected to an applied elongation, the web materials extend in the direction of applied elongation. When the applied elongation is released, the web materials return to a substantial degree to their untensioned condition. While such web materials exhibiting an elastic-like behavior have a wide range of utility (for example, durable articles of apparel, disposable articles of apparel, covering materials such as upholstery, wrapping materials for complex shapes, and the like), they are particularly well suited for use as top sheets, back sheets, absorbent cores, and absorbent articles and for materials suitable for the containment of matter.

SUMMARY OF THE INVENTION

In accordance with one aspect of the invention, a web material is provided comprising first and second precursor webs. The first and second precursor webs comprise a polymeric film material. Further, the web material has a first side comprising the first precursor web and at least one protuberance disposed thereon. Each of the protuberances comprises the second precursor web, wherein the protuberances are integral extensions of the second precursor web extending through the first precursor web. The web material further comprises a second side comprising the second precursor web.

In accordance with another aspect of the invention, a web material for a container is claimed. The web material comprises first and second precursor webs. The first precursor web comprises a polymeric film material. The web material has a first side comprising the first precursor web and at least one protuberance disposed thereon. Each of the protuberances comprises the second precursor web, wherein the protuberances are integral extensions of the second precursor web extending through the first precursor web. The web material further comprises a second side comprising the second precursor web. The web material forms a semi-enclosed container having an opening defined by a periphery and an opening plane. The container is expandable in response to forces exerted by contents within the container to provide an increase in volume of the container such that the container accommodates the contents placed therein.

DETAILED DESCRIPTION OF THE INVENTION

Figure 1:
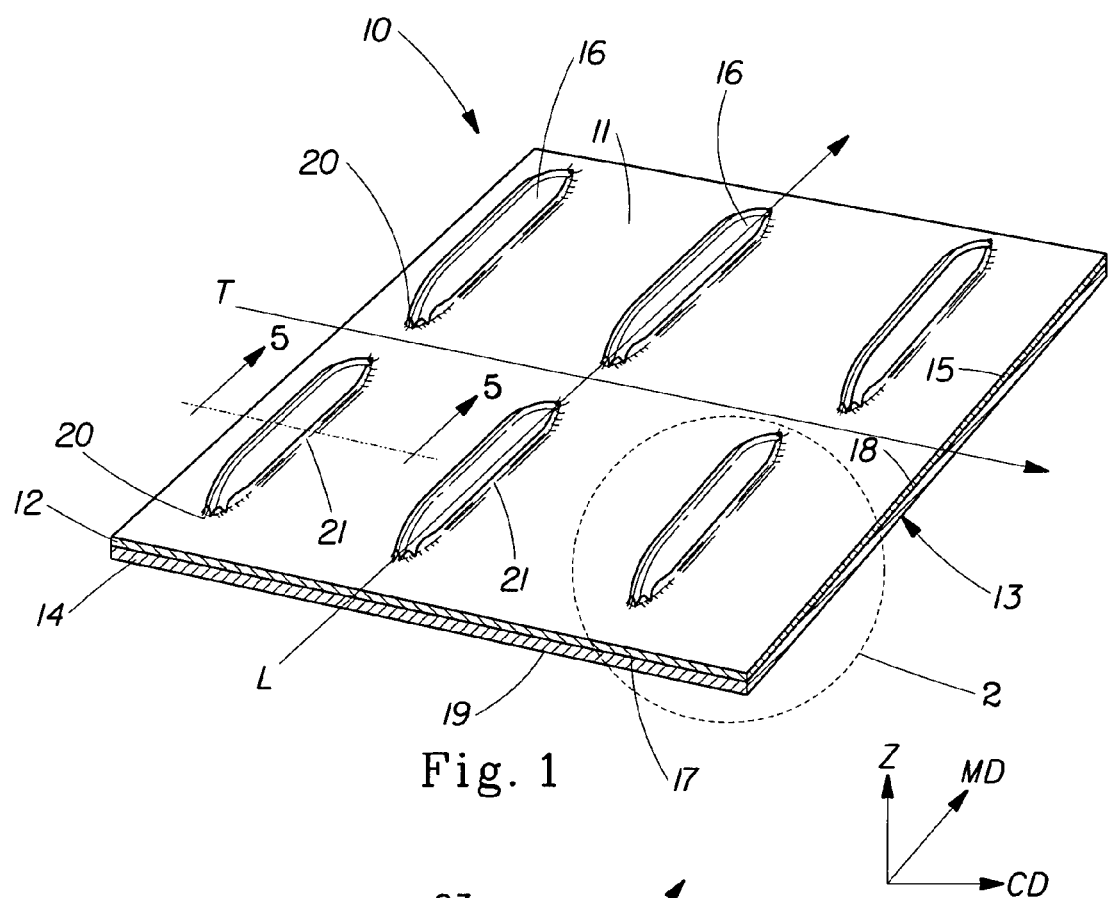
FIG. 1 is a perspective view of an exemplary web of the present invention.

As shown in FIG. 1, the present invention provides a laminated structurally elastic-like web substrate 10 (hereinafter referred to simply as web substrate 10. Web substrate 10 comprises at least two layers. The layers are referred to herein as generally planar, two-dimensional precursor webs, such as first precursor film 12 and second precursor film 14.

Although the precursors are described and referred to herein as films, either precursor can be a film material, a non-woven material, pre-apertured web, a woven web material, inks, ink-like materials, coatings, combinations thereof, or the like. First precursor film 12 and second precursor film 14 can be joined by adhesive, thermal bonding, ultrasonic bonding, combinations thereof, and the like, but are preferably joined without the use of adhesive or other forms of bonding. Alternatively, first precursor film 12 and second precursor film 14 can be provided as a coextruded film material, as would be known to one of skill in the art using the above-mentioned materials. As disclosed below, the constituent precursor films of web 10 can be joined by interlocking mechanical engagement resulting in the formation of protuberances 16.

Web substrate 10 has a first side 11 and a second side 13, the term "sides" being used in the common usage of generally planar two-dimensional webs, such as paper and films that have two sides when in a generally flat condition. Each precursor film 12, 14 has a first surface 15,18, respectively, and a second surface 17, 19, respectively. Web substrate 10 has a machine direction (MD) and a cross-machine direction (CD) orthogonal and co-planar thereto, as is commonly known in the art of web manufacture. Web substrate 10 also has a Z-direction orthogonal to both the MD and CD. Although the present invention can be practiced with woven and non-woven web materials, in a most preferred embodiment, first precursor film 12 is provided as a polymeric film, ink, ink-like material, coating, combinations thereof, or the like. Further, second precursor film 14 can be a woven or non-woven web material but is most preferably provided as a polymeric film. Similarly, first precursor film 12 and second precursor film 14 may be similar or dissimilar materials, apertured polymeric films, co-extruded polymeric film, combinations thereof, or the like.

In a preferred embodiment, first side 11 of web substrate 10 is defined by exposed portions of the first surface 15 of first precursor film 12 and at least one but preferably a plurality of discreet protuberances 16 which are integral extensions of the polymeric film of second precursor film 14 extending through first precursor film 12. Each protuberance 16 can comprise an elongate open and/or closed loop of polymeric film extending through first precursor film 12 and outwardly from the first surface 11 thereof. Alternatively, each protuberance 16 can be a single closed protrusion of polymeric film material from second precursor film 14 that extends outwardly from the first surface 11 of first precursor film 12. Additionally, there can be a combination of elongate loops and closed protrusions of polymeric film material from second precursor film 14 that extends outwardly from the first surface 11 of first precursor film 12.

Figure 2:
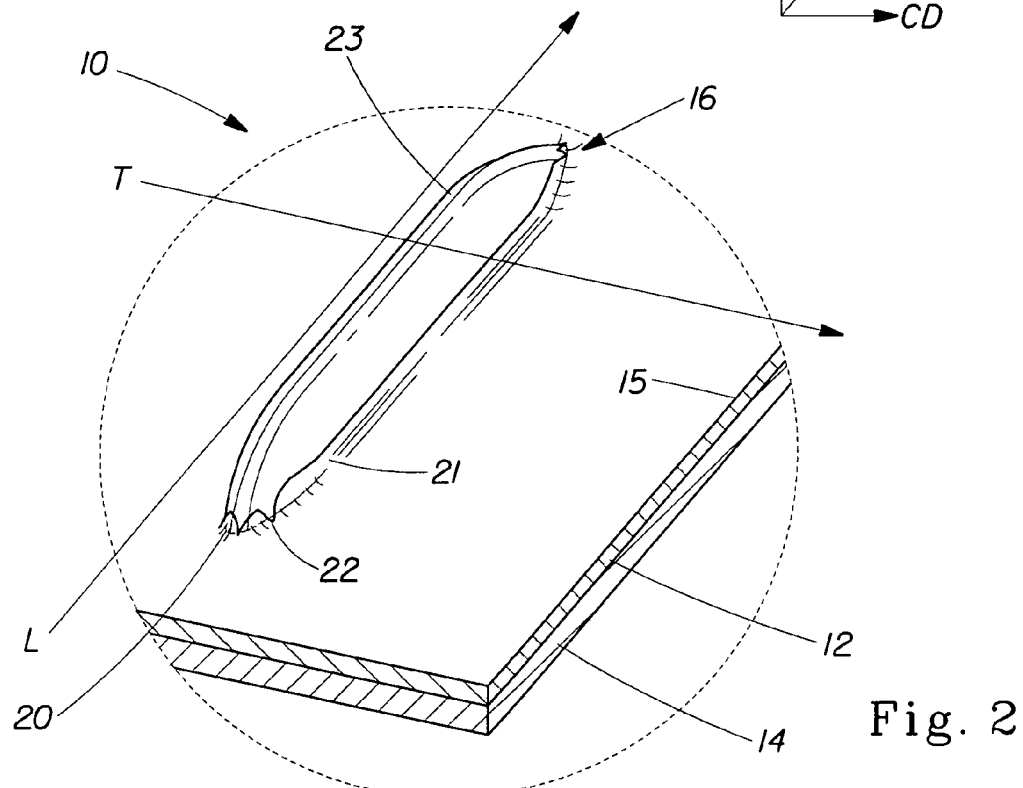
FIG. 2 is an enlarged view of a portion of the web shown in FIG. 1.
Figure 3:
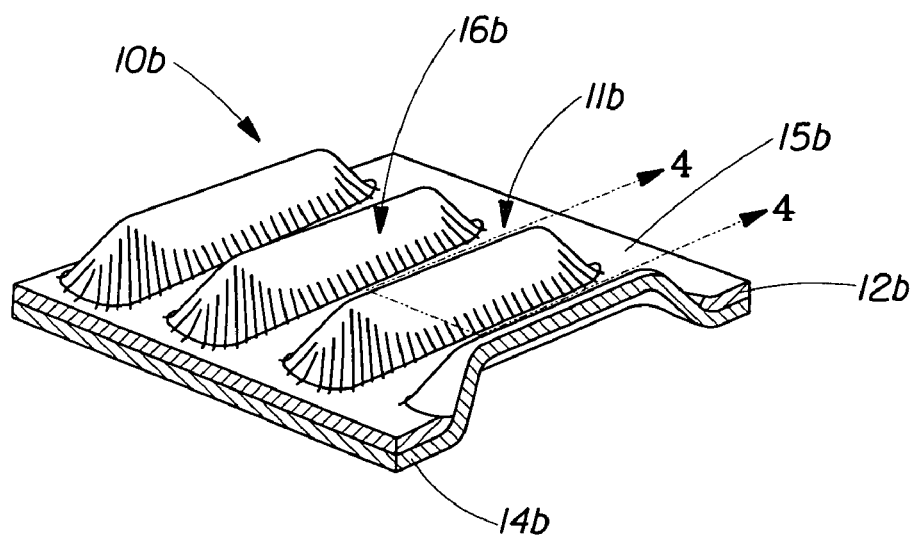
FIG. 3 is a perspective view of another embodiment of an exemplary web.
Figure 4:
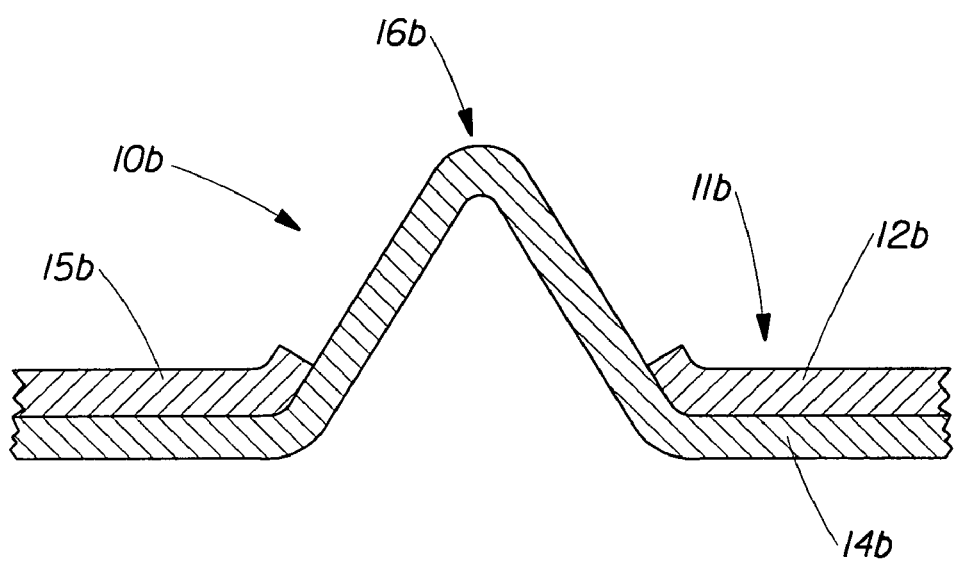
FIG. 4 is a cross-sectional view of the section labeled 4-4 of FIG. 3.
Figure 5:
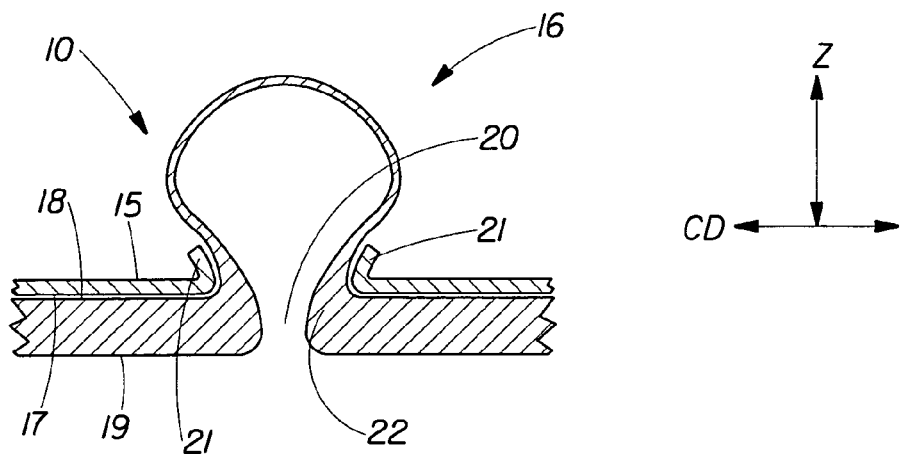
FIG. 5 is a cross-sectional view of the section labeled 5-5 of FIG. 1.

As shown in FIG. 3, an alternative preferred embodiment can provide first side 11b of web substrate 10b to be defined by exposed portions of the first surface 15b of first precursor film 12b and at least one but preferably a plurality of discreet protuberances 16b that are integral extensions of the polymeric film of second precursor film 14b extending through first precursor film 12. Each protuberance 16b can comprise an elongate "tent-like" structure of polymeric film extending through first precursor film 12b and outwardly from the first surface 11b thereof. Alternatively, each protuberance 16b can be a single closed protrusion of polymeric film material from second precursor film 14b that extends outwardly from the first surface 11b of first precursor film 12b. Additionally, there can be a combination of "tent-like structures" and closed protrusions of polymeric film material from second precursor film 14b that extends outwardly from the first surface 11b of first precursor film 12b. One skilled in the art can realize that the embodiments depicted in FIG. 1 and FIG. 3 are similar representation and further discussion will refer to the drawings interchangeably unless were specifically noted. As shown in FIGS. 2 and 5, each protuberance 16 can comprise portions of second precursor film 14 extending through first precursor film 12 and outwardly from the first surface 15 thereof. Alternatively, as shown in FIG. 4, each protuberance 16b can comprise portions of second precursor film 14b extending through first precursor film 12b and outwardly from the first surface 15 thereof. One skilled in the art can realize that the embodiments depicted in FIG. 2 and FIG. 4 could be considered similar representations. Therefore, any further discussion regarding the web substrate 10 of the present invention can refer to FIGS. 1/2 and 3/4 interchangeably, unless noted otherwise.

The basis weight of laminate webs suitable for use in the present invention can range from 10 $g/m^2$ to 1,000 $g/m^2$, preferably 15 $g/m^2$ to 250 $g/m^2$, and most preferably 15 $g/m^2$ to 35 $g/m^2$ depending on the ultimate use of web material 10. For use as a trash-retaining receptacle, for example, both first precursor film 12 and second precursor film 14 can comprise polymeric web materials. The resulting trash retaining receptacle has a basis weight ranging from between 15 $g/m^2$ to 100 $g/m^2$. For use as a diaper backsheet, first precursor film 12 and second precursor film 14 can have a combined basis weight ranging from between 15 $g/m^2$ and 62 $g/m^2$.

As used herein, the term "polymer" generally includes, but is not limited to, homopolymers, copolymers such as, for example block, graft, random, and alternating copolymers, terpolymers, etc. and blends and modifications thereof. In addition, unless otherwise specifically limited, the term "polymer" also includes all possible geometric configurations of the material. The configurations include, but are not limited to, isotactic, atactic, syndiotactic, and random symmetries. One of skill in the art will realize that the present invention would also be suitable for use with spun bond fibers, melt blown fibers, monocomponent fibers, bicomponent fibers, biconstituent fibers, non-round fibers, and other materials having properties suitable for use with the present invention. As one of skill in the art would know, exemplary polymers include polyvinyl chloride (PVC), polyvinylidene chloride (PVDC), and any polyolefin such as linear low density polyethylene (LLDPE), high density polyethylene (HDPE) or polypropylene and blends thereof, polyesters, and polyurethanes, and any combinations thereof.

Referring again to FIG. 1, the number, spacing, and dimensions of protuberances 16 can be varied to provide any desired characteristics to first side 11 of web substrate 10, such as texture. For example, if protuberances 16 are sufficiently closed spaced, the first side 11 of web substrate 10 can have a cloth-like feel. Alternatively, protuberances 16 can be arranged in patterns, such as lines or filled shapes, to create portions of a structure having greater texture, softness, bulk, absorbency, or visual design appeal. For example, when protuberances 16 are arranged in a pattern of a line or lines, the protuberances 16 can have the appearance of stitching. Protuberances 16 can also be arranged to form specific shapes, such as designs, words, or logos. Such shapes can be used, for example, on laminates useful for trash disposal bags and the like. Likewise, the size dimensions, such as the height, length, and width of individual protuberances 16, can be varied.

Second precursor film 14 is preferably a polymeric web or substrate having sufficient elongation properties to have portions formed into protuberances 16, as described below.

Protuberances 16 are formed by displacing polymeric material out of plane in the Z-direction at discreet localized portions of second precursor film 14. More often, however, for most polymeric first precursor webs 14, a displacement out of plane in the Z-direction is due to portions of the web material in the form of protuberances 16 having been at least partially plastically stretched and permanently deformed in the Z-direction to form protuberances 16. Therefore, in one embodiment, depending on the desired height of each protuberance 16, the constituent polymeric material of the second precursor film 14 can exhibit an elongation to break of at least about 5%, more preferably at least about 10%, or preferably at least about 25%, even more preferably at least about 50%, and most preferably at least about 100%. Elongation to break can be determined by tensile testing, such as by use of Instron® tensile testing equipment, as known to those of skill the art, and can be generally found on material data sheets from suppliers of such polymeric or web materials. Further, it can be appreciated that a suitable second precursor film 14 should comprise materials capable of experiencing sufficient plastic deformnation and tensile elongation such that protuberances 16 are formed.

Additionally, second precursor film 14 can be a polymeric web material comprising elastic or elastomeric materials. Elastic or elastomeric materials can be stretched at least about 50% and retumn to within 10% of their original dimension. Protuberances 16 can be formed from such elastic materials if the elastic materials are simply displaced due to their irnmobility within the polymeric material, or if the elastic fibers are stretched beyond their elastic limit and are plastically deformed.

First precursor film 12 can be virtually any continuous or discontinuous web material having sufficient integrity to be formed into a laminate and sufficiently less elongation properties relative to the second precursor film 14, such that upon experiencing the strain of material from second precursor film 14 being urged out of plane in the Z-direction of first precursor film 12, first precursor film 12 will rupture. For example, first precursor film 12 will tear due to extensional failure such that portions of the second precursor film 14 can extend through (i.e., "punch through") first precursor film 12 to form protuberances 16 on first side 11 of web substrate 10. Preferably, first precursor film 12 is a polymeric film. However, as would be known to one of skill in the art, first precursor film 12 can also be a woven textile web, a-non-woven web, a polymer film, an apertured polymer film, a paper web, a metal foil, a foam, coating, printing, combinations thereof, or the like. A representative protuberance 16 for the embodiment of web substrate 10 shown in FIG. 1 is shown in a further enlarged view in FIG. 2. As shown in FIG. 2, protuberance 16 comprises a single protuberance 16 of film material that is substantially aligned such that protuberances 16 have a distinct linear orientation in a longitudinal axis L. Protuberances 16 also have a transverse axis T generally orthogonal to longitudinal axis L in the machine direction/cross-machine direction plane. As shown in FIG. 1, longitudinal axis L is parallel to the machine direction. In one embodiment, all of the spaced apart protuberances have generally parallel longitudinal axis L. The number of protuberances 16 per unit area of web substrate 1 (i.e., the area density of protuberances 16) can be varied from 1 protuberance per square inch to as high as 155 protuberances/cm$^2$. In a preferred embodiment, there is at least 0.2 protuberances/cm$^2$, preferably at least 8 protuberances/cm$^2$, and most preferably at least 15.5 protuberances/cm$^2$. As would be known to one of skill the art, the area density need not be uniform across the entire area of web substrate 16; however, protuberances 16 can be only in certain regions of the web substrate 10, such as in regions have predetermined shapes, such as lines, stripes, bands, circles, and the like.

Alternatively, first precursor film 12 can be any continuous or discontinuous web material, having sufficient integrity to be formed into a laminate having sufficiently less elongation properties relative to the second precursor film 14, that upon experiencing the strain of material from second precursor film 14 being urged out of plane in the Z-direction of first precursor film 12, will thin relative to said second precursor film 14. One skilled in the art will realize that this embodiment is dependant on the degree of strain induced by the urging of the second precursor film 14 out of plane and will occur at lower induced strains than in the embodiment described above. In certain embodiments it is advantageous to thin first precursor film 12 without rupture. This allows for continued barrier properties but can result in relative opacity reduction, assuming no crazing, in first precursor film 12. This can allow for color differences between the protuberance 16 and the bulk of the remaining web 10 due to the opacity change, especially when second precursor film 14 is a different color or shade than first precursor film 12. Additionally it can modify the rate of transport of actives or cause their activation due to thinning, while maintaining barrier properties.

As shown in FIGS. 1 and 2, protuberances 16 extend through openings 20 in first precursor film 12. Openings 20 are formed by locally rupturing first precursor film 12 by the process described in detail below. Rupture may involve a simple splitting open of first precursor film 12 such that opening 20 remains a simple two-dimensional aperture. However, for some materials, such as polymer films, portions of first precursor film 12 can be deflected or urged out of plane (i.e., the plane of first precursor film 12) to form flap-like structures or flaps 21. The form and structure of flaps 21 can be highly dependent upon the material properties of first precursor film 12. Flaps 21 can have the general structure of one or more flaps, as shown in FIGS. 1 and 2. In other embodiments, flap 21 can have a more volcano-like structure, as if the protuberance 16 is erupting from the flap 21. In yet other embodiments, flap 21 may at least partially cover protuberance 16 in an umbrella-like fashion.

In one embodiment, flaps 21 do not contribute significantly to the material of protuberances 16 and particularly do not contribute significantly to any tactile quality of protuberance 16. In one embodiment, therefore, the web substrate 10 comprises at least two layers (i.e., precursor webs 12 and 14) but at least one of the layers (i.e., first precursor film 12 in FIGS. 1-2) does not significantly affect the tactile qualities of protuberances 16.

In one embodiment, flaps 21 may extend out of plane as far as, or further than, the protuberances 16 themselves extend out of the plane of web substrate 10. In this embodiment, flaps 21 can cause the protuberances 16 to be more resilient and less susceptible to flattening due to compressive or bending forces. In one embodiment, therefore, the web substrate 10 comprises at least two layers (i.e., first precursor film 12 and second precursor film 14) and both layers can affect any tactile or compressive qualities of protuberances 16.

Protuberances 16 are protrusions of second precursor film 14 that preferably extend through first precursor film 12 and can be locked in place by frictional engagement with material from flaps 21 that form the openings 20. In some embodiments, for example, lateral width of openings 20 (i.e., the dimension measured parallel to its transverse axis)

can be less than the maximum width of the tooth that formed the opening, as described below. This indicates a certain amount of recovery at the opening that tends to constrain protuberance 16 from pulling back out through openings 20. The frictional engagement of the protuberances 16 and openings 20 provides for a laminate web structure 10 having permanent structures in the form of protuberances 16 on one side that can be formed without adhesives or thermal bonding.

From the description of web substrate 10 comprising a polymeric second precursor film 14, it can be seen that the polymer comprising protuberance 16 can originate and extend from either the first surface 18 or the second surface 19 of second precursor film 14. Of course, the polymer comprising protuberance 16 can also extend from the interior 17 of first precursor film 12. When web substrate 10 is formed from a co-extruded polymeric material, it should be realized that first surface 18 and the interior 17 could be in intimate contact. As shown in FIGS. 1 and 2, the polymer comprising protuberances 16 extends due to having been urged out of the generally two-dimensional plane of second precursor film 14 (i.e., urged in the Z-direction). In general, the polymer comprising protuberances 16 comprises material that is integral with and extends from the polymer of the second precursor film 14.

Therefore, from the above descriptions, it is understood that in one embodiment web substrate 10 can be described as being a laminate formed by selected mechanical deformation of at least a first and second precursor webs, at least the first precursor web being a polymeric web, the laminate web having a first side, the first side comprising the second precursor web and a plurality of discreet protuberances, each of the discreet protuberances comprising polymeric material being integral extensions of the second precursor web and extending through the first precursor web, and a second side, the second side comprising the second precursor web.

The extension of polymeric material from second precursor film 14 through first precursor film 12 to form protuberance 16 can be accompanied by a general reduction in polymeric web substrate cross-sectional dimension due to plastic deformation of the polymer and Poisson's ratio effects. The polymeric material comprising protuberance 16 can have an average thickness less than the average thickness of the polymeric material comprising second precursor film 14. One effect believed to occur from this thinning of polymeric material is a perceived softness of the first side 11 of web substrate 10. It has been found that often the reduction in cross-sectional thickness is greatest intermediate base 22 and the distal portion 23 of protuberance 16. This is believed to be due to the preferred method of making the web substrate 10 as will be disclosed more fully below. Some portions of the second precursor film 14 may laterally squeeze the base 22 of the protuberance 16. The base 22 of the protuberance 16 may even be closed if the material from the protuberance 16 is close enough to get it to touch or may remain open. The closing or narrowing or squeezing of other material at the base 22 can help stabilize the protuberances 16 and first precursor film 12.

Further, providing discreet protuberances comprising polymeric material as integral extensions of the second precursor film 14 extending through first precursor film 12 can provide web substrate 10 with at least two different stages of resistive force to an applied axial elongation. This can occur along at least one axis when web substrate 10 is subjected to the applied elongation in a direction parallel to the axis in response to an externally applied force upon web substrate 10.

Figure 9:
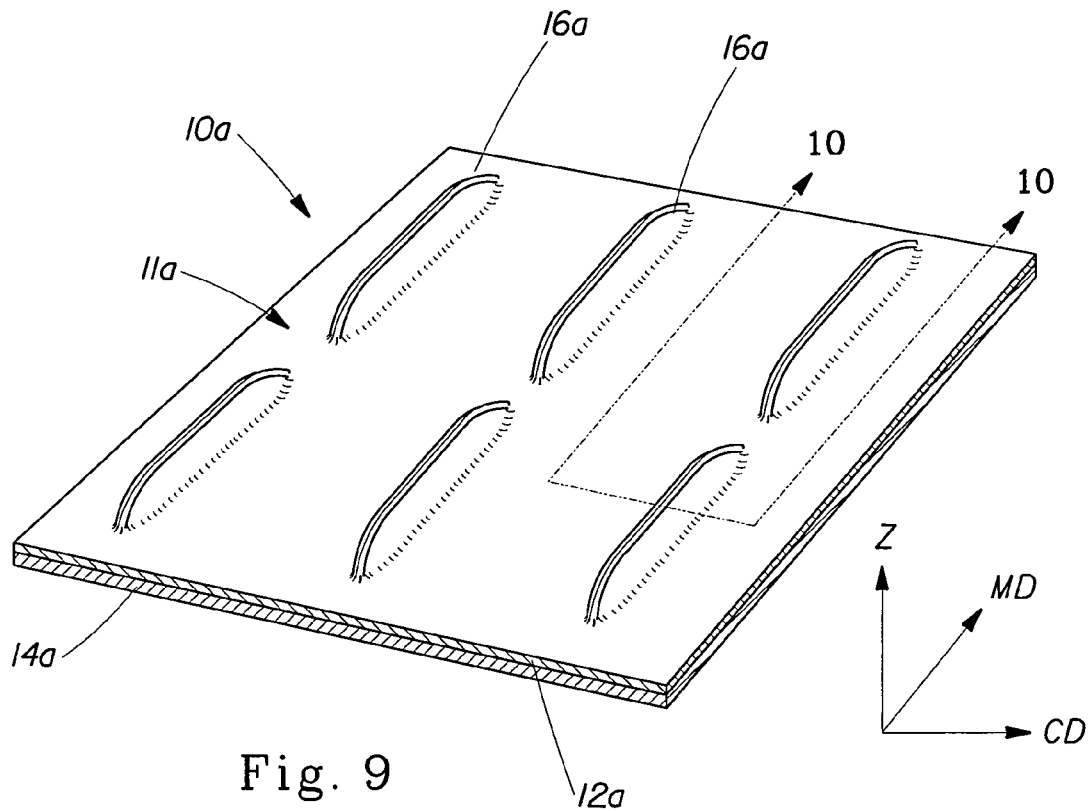
FIG. 9 is a perspective view of an alternative embodiment of an exemplary web; and, FIG. 10 is a cross-sectional view of the section labeled 10-10 of FIG. 9.

Shown in FIG. 9, an alternative embodiment of web material 10a can comprise second precursor film 14a. Second precursor film 14a can be provided as virtually any continuous or discontinuous web material having sufficient integrity to be formed into a laminate wherein second precursor film 14a has less elongation properties relative to the first precursor film 12a. In this way, a force applied to second precursor film 14a urging second precursor film 14a out of plane in the Z-direction with first precursor film 12a can cause second precursor film 14a to rupture. For example, second precursor film 14a can tear due to extensional failure while portions of the first precursor film 12a can extend to form protuberances 16a on first side 11a of web substrate 10a. Preferably, first precursor film 12a is a polymeric film. However, as would be known to one of skill in the art, first precursor film 12a can also be a woven textile web, a non-woven web, a polymer film, an apertured polymer film, a paper web, a metal foil, a foam, coating, printing, combinations thereof, or the like.

Figure 8:
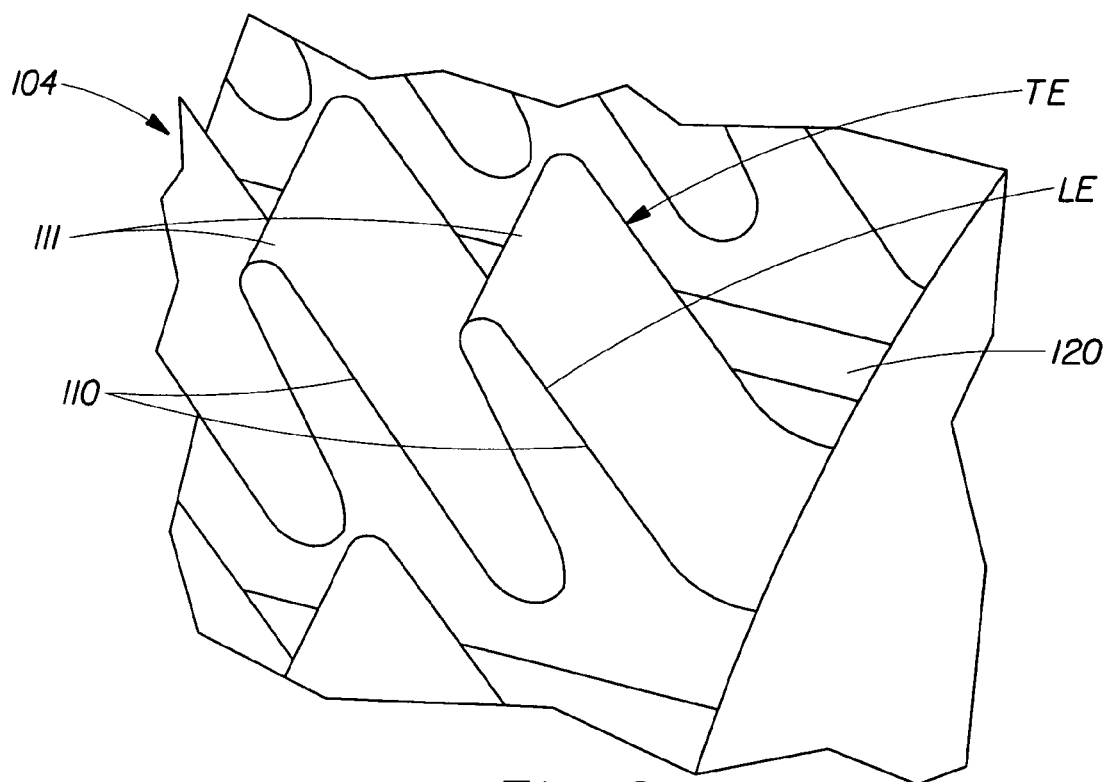
FIG. 8 is an enlarged perspective view of a portion of the apparatus for forming the web of the present invention.
Figure 10:
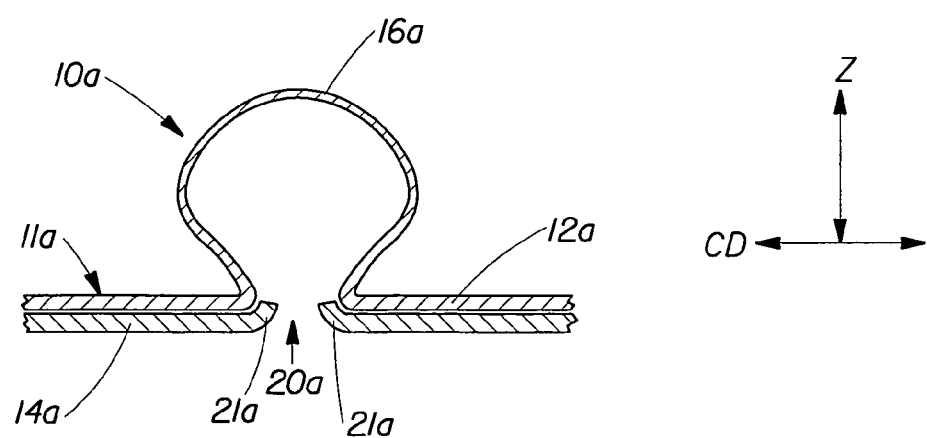

As shown in FIG. 10, protuberances 16a extend adjacent to openings 20a in second precursor film 14a. Openings 20a are formed by locally rupturing second precursor film 14a. Such a rupture may involve a simple splitting open of first precursor film 14a so that opening 20a remains a simple two-dimensional aperture. However, for some materials, such as polymer films, portions of second precursor film 14a can be deflected or urged out of plane (i.e., the plane of second precursor film 14a) to form flap-like structures or flaps 21a. The form and structure of flaps 21a can be highly dependent upon the material properties of second precursor film 14a. Flaps 21a can have the general structure of one or more flaps, as shown in FIG. 8. In other embodiments, flap 21a may at least partially cover the inside surface of protuberance 16a in an igloo-like fashion.

In accordance with the embodiment shown in FIGS. 9 and 10, protuberances 16a can be provided with and/or contain active compositions on either surface of protuberance 16a. When located on the inner surface of protuberances 16a (i.e., disposed between first precursor film 12a and second precursor film 14a), protuberances 16a could be partially or completely filled with an active composition. Exemplary, but non-limiting active compositions can include such items as powders, lotions, emulsions, gels, adhesive, paint, icing, inks, dyes, combinations thereof, and the like. Such active compositions could be used as deodorizing, odor absorbing, liquid absorbing, antibacterial, cleaning, bleaching, whitening, decorating, paint, icing, combinations thereof, and the like.

Alternatively, flaps 21a can cover opening 20a protecting the above active compositions until required by a user. Flaps 21a could act as a valve, dispensing or metering any active compositions out from the internal space of protuberance 16a and/or containing them within the internal space of protuberance 16a as required. Methods for dispensing an active composition from within protuberance 16a can include external forces pushing upon protuberance 16a such as physical contact force or pressure, heating the active composition so its viscosity changes allowing it to flow out of protuberance 16a, applying an external vacuum that could pull an active composition out of protuberances 16a, capillary action pulling an active composition out of protuberance 16a, a magnetic action pulling an active composition out of protuberance 16a, combinations thereof, and the like.

Figure 6:
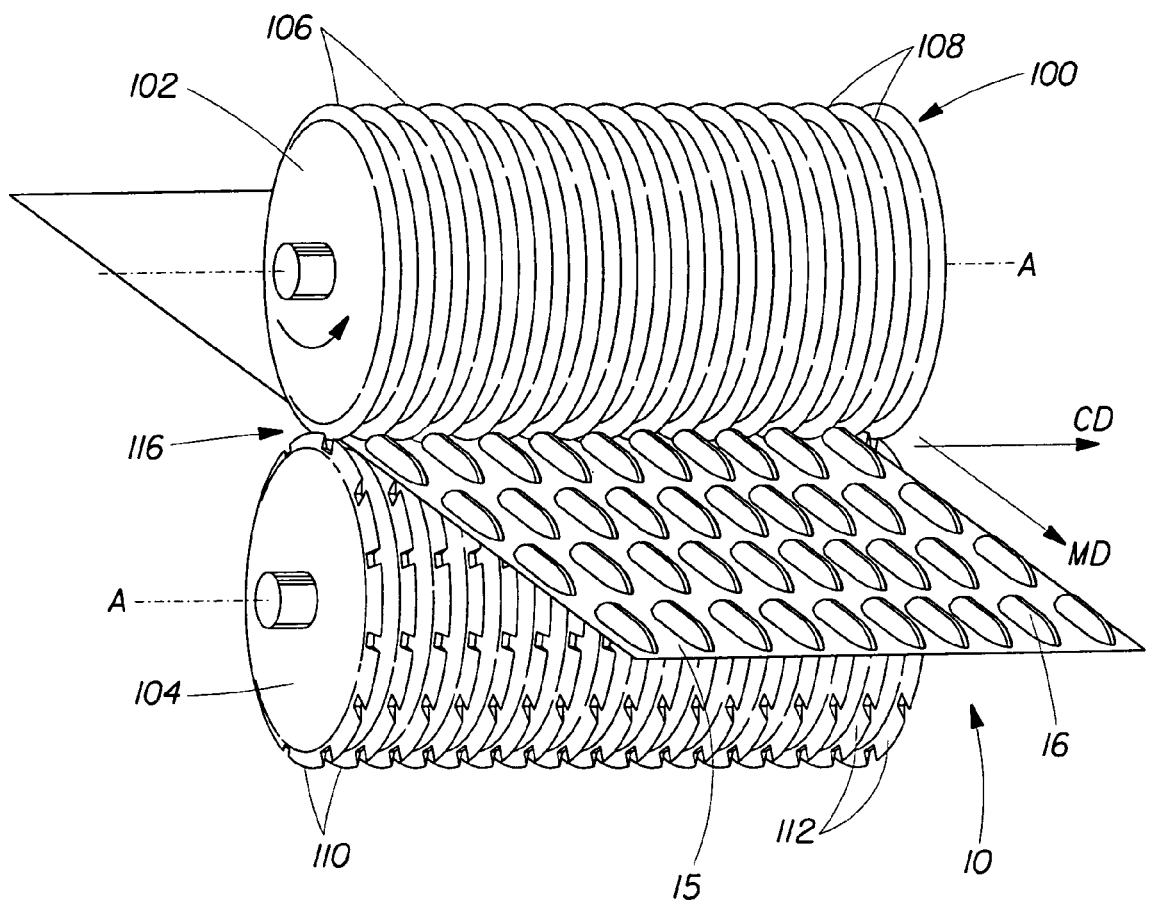
FIG. 6 is a perspective view of an apparatus for forming the web of the present invention.

Referring to FIG. 6, there is shown an apparatus and method for making web substrate 10 of the present invention. The apparatus 100 comprises a pair of intermeshing rolls 102 and 104, each rotating about an axis A, the axis, A, being parallel in the same plane. Roll 102 comprises a plurality of ridges 106 and corresponding grooves 108, which extend unbroken about the entire circumference of roll 102. Roll 104 is similar to roll 102 but rather than having ridges that extend unbroken about the entire circumference, roll 104 comprises a plurality of circumferentially extending ridges that have been modified to be rows of circumferentially spaced teeth 110 that extend in spaced relationship about at least a portion of roll 104. The individual rows of teeth 110 of roll 104 are separated by corresponding grooves 112. In operation, rolls 102 and 104 intermesh so that the ridges 106 of roll 102 extend into the grooves 112 of roll 104 and the teeth 110 of roll 104 extend into the grooves 108 of roll 102. The intermeshing is shown in greater detail in the cross-sectional representation of FIG. 5 discussed below. Both or either of rolls 102 and 104 can be heated by means known in the art, such as by using hot oil-filled rollers, electrically heated rollers, cartridge heaters, and the like.

The apparatus 100 is shown in a preferred configuration having one patterned roll (e.g., roll 104) and one non-patterned grooved roll 102. However, in certain embodiments, it may be preferable to use two patterned rolls 104 having either the same or differing patterns on the same or different corresponding regions of the respective rolls. Such an apparatus can produce web materials 10 with protuberances 16 protruding from both sides of the web substrate 10. An apparatus could also be designed to have teeth that point in opposite directions on opposing rolls. This would result in a web material 10 with protuberances 16 being produced on both sides of the web substrate 10.

Web substrate 10 can be manufactured with a continuous process by mechanically deforming precursor webs such as first precursor film 12 and second precursor film 14 that can each be described as generally planar and two-dimensional prior to processing by the apparatus shown. By "planar" and "two-dimensional," it is meant that the webs start the process in a generally flat condition relative to the finished web substrate 10 that has distinct out-of-plane Z-direction three-dimensionality due to the formation of protuberances 16. "Planar" and "two-dimensional" are not to define or imply any particular flatness, smoothness, or dimensionality herein. As known to one of skill the art, web substrate 10 can be manufactured in a continuous process using materials that are generally non-planar in orientation with respect to each other or the final web substrate 10.

Alternatively, the process and apparatus of the present invention are similar in many respects to a process described in U.S. Pat. No. 5,518,801 and are generally referred to in the patent literature as structurally elastic-like films. However, there are differences between the apparatus and process of the present invention and the apparatus and process disclosed in the '801 patent, and the differences are apparent in the respective webs produced thereby. As described below, the teeth 110 of roll 104 have a specific geometry associated with leading and trailing edges that permit the teeth to essentially punch through the first precursor film 12 rather than deforming the web. In a two-layer laminate system forming web substrate 10, the teeth 110 urge polymer from the second precursor film 14 simultaneously out of plane and through first precursor film 12 which is punctured, so to speak, by the teeth 110 pushing the material from second precursor film 14 through first precursor film 12 to form protuberances 16. Therefore, a web substrate 10 of the present invention can have protuberances 16 of continuous ends or tunnel-like protuberances 16 extending through and away from the first surface 15 of first side 11.

Referring again to FIG. 6, first precursor film 12 and second precursor film 14 can be provided either directly from the respective web making processes, directly from a web coating or printing process, or indirectly from supply rolls, and moved in the machine direction to the nip 116 of counter rotating intermeshing rolls 102 and 104. First precursor film 12 and second precursor film 14 are preferably held in a sufficient web tension so as to enter the nip 116 in a generally flattened condition by means well known in the art of web handling. As first precursor film 12 and second precursor film 14 go through the nip 116, the teeth 110 of roll 104 which are intermeshed with grooves 108 of roll 102 simultaneously urge portions of second precursor film 14 onto the plane of second precursor film 14 and through first precursor film 12 to form protuberances 16. In effect, teeth 110 push and/or punch polymeric material, comprising second precursor film 14 through first precursor film 12.

As the tip of teeth 110 push through first precursor film 12 and second precursor film 14, the portions of the polymeric material of second precursor film 14 are oriented predominantly in the cross-machine direction, the cross teeth 110 are urged by the teeth 110 out of the plane of second precursor film 14. Polymeric material of second precursor film 14 can be urged out of plane due to stretching and/or plastically deforming in the Z-direction. Portions of the second precursor film 14, urged out of plane by teeth 110 push through first precursor film 12 which is due to its relatively lower extensibility, ruptures thereby resulting in formation of protuberances 16 on first side 15 of web substrate 10. Material comprising second precursor film 14 that are predominantly oriented generally parallel to the longitudinal axis L (i.e., in the machine direction of second precursor film 14, as shown in FIG. 1) are spread apart by teeth 110.

It can be appreciated by the foregoing description that when web material 10 is made by the apparatus and method of the present invention that first precursor film 12 and second precursor film 14 should possess differing material properties with respect to the ability of the precursor webs through elongate before failure (e.g., failure due to tensile stresses). In particular, a polymeric second precursor film 14 can have greater elongation characteristics relative to first precursor film 12 such that the material thereof can move or stretch sufficiently to form protuberances 16 while the first precursor film 12 may or may not rupture (i.e., may or may not stretch to the extent necessary to form protuberances 16). In other words, upon sufficient force applied to second precursor film 14, the material therein tends to extend while the material of first precursor film 12 is unable to extend and tends to break.

For a given maximum strain (e.g., the strain imposed by teeth 110 of apparatus 100), first precursor film 12 must actually fail under the tensile loading produced by the imposed strain; that is, for the protuberances 16 of the present invention to be disposed on the first side 15 of web material 10, first precursor film 12 must have sufficiently low elongation to break such that it locally (i.e., in the area of strain) fails in tension, thereby producing openings 20 through which protuberances 16 can extend. In one embodiment, first precursor film 12 has an elongation to break in the range of 1% to 5%. While the actual required elongation to break depends on the strain to be induced to form web material 10, it is recognized that for most embodiments first precursor film 12 can exhibit a web elongation to break of 6% or more. It is also recognized that actual elongation to break can depend on the strain rate, which, for the apparatus shown in FIG. 5, is a function of line speed. Elongation to break of web materials used in the present invention can be measured by means known to those of skill in the art, such as by standard tensile testing methods, for example ASTM D882-95, using standard tensile testing apparatii, such as those manufactured by Instron®, MTS®, Thwing-Albert®, and the like.

Furthermore, relative to second precursor film 14, first precursor film 12 can have lower elongation to break so that rather than extending out of plane to the extent of the protuberances 16, first precursor film 12 fails in tension under the strain produced by the formation of protuberances 16 (e.g., by the teeth 110 of apparatus 100). In one embodiment, first precursor film 12 exhibits sufficiently low elongation to break relative to second precursor film 14, such that flaps 21 of opening 20 only extend slightly out of plane, if at all, relative to protuberances 16.

Additionally, the number, spacing, and size of protuberances 16 can be varied by changing the number, spacing, and size of teeth 110 and making corresponding dimensional changes, as necessary, to roll 104 and/or roll 102. This variation together with the variation possible in first precursor film 12 and second precursor film 14 permits many varied web materials 10 to be made for many purposes.

Figure 7:
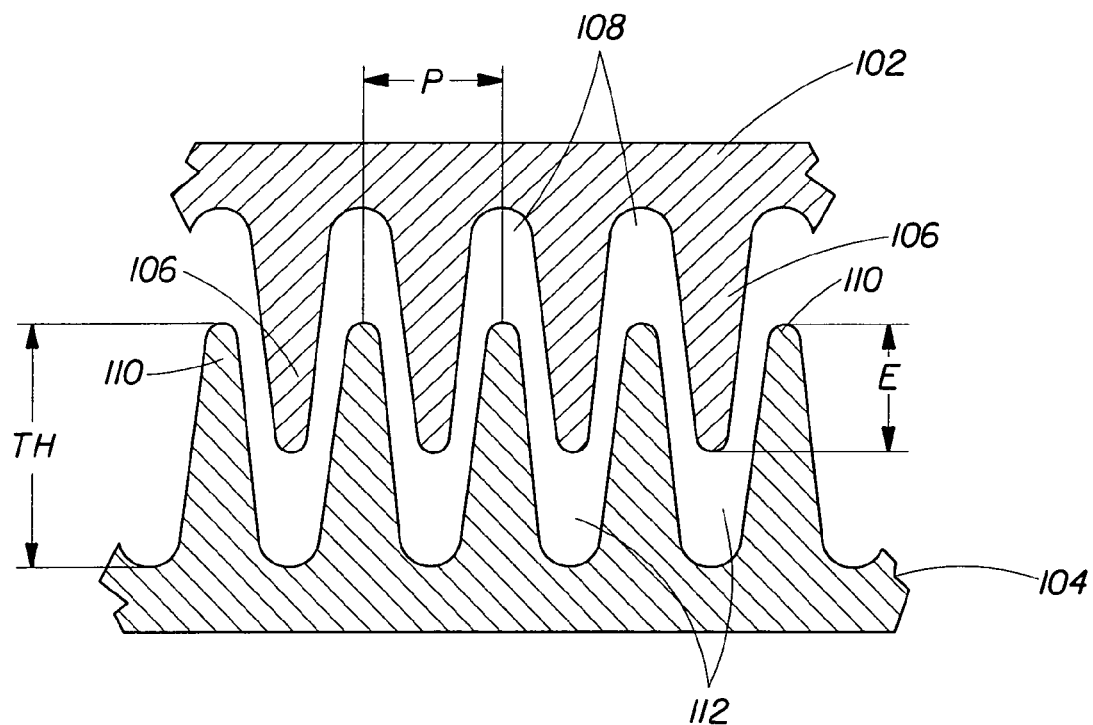
FIG. 7 is a cross-sectional depiction of a portion of the apparatus shown in FIG. 6.

FIG. 7 shows a cross-sectional portion of the intermeshing rolls 102 and 104 and ridges 106 and teeth 110. As shown, teeth 110 have a tooth height (TH). (Note that TH can also be applied to ridge height. In a preferred embodiment, tooth height and ridge height are equal). Tooth-to-tooth spacing (or ridge-to-ridge spacing) is referred to as the pitch (P). As shown, depth of engagement (E) is a measure of the level of intermeshing the rolls 102 and 104 and is measured from tip of ridge 106 to tip of tooth 110. The depth of engagement E, tooth height TH, and pitch height (P) can be varied as desired, depending on the properties of first precursor film 12 and second precursor film 14 and the desired characteristics of resulting web material 10. For example, in general, the greater the level of engagement E, the greater the necessary elongation properties second precursor film 14 must possess to prevent rupture of second precursor film 14. Also, the greater the density of protuberances 16 desired, the smaller the pitch should be and the smaller the tooth length TL and tooth distance TD should be, as described below.

Exemplary teeth 110, useful in the present invention, are shown in FIG. 8. In this embodiment, roll 104 and teeth 110 have a uniform circumferential length dimension (TL) measured generally from the leading edge (LE) to the trailing edge (TE) at the tooth tip 111 and are uniformly spaced from one another circumferentially by distance (TD). As would be known to one of skill in the art, the variables E, P, TH, TD, and TL can be varied independently of each other to achieve the desired size, spacing, and area density of protuberances 16.

As shown in FIGS. 8, each tooth 110 has a tip 111, a leading edge LE and a trailing edge TE. The tooth tip 111 is elongate and has a generally longitudinal orientation corresponding to longitudinal axis L of protuberances 16. In a preferred embodiment, the leading edge LE and trailing edge TE should be very nearly orthogonal to the local peripheral surface 120 of roll 104. However, the transition from the tip 111 and the leading edge LE or trailing edge TE could be provided with a large angle resulting in a sufficiently large radius of curvature in the transition from the tip 111 to leading edge LE or trailing edge TE such that teeth 110 do not push through first precursor film 12 at the leading LE and trailing edge TE. Use of tooth designs with sufficiently large radius of curvature in the transition could result in structures as depicted in FIGS. 1-4, however predominantly as shown in FIGS. 3-4. Alternatively, the transition from the tip 111 to leading edge LE or trailing edge TE could be a sharp angle, such as a right angle having a sufficiently small radius of curvature such that teeth 10 push through first precursor film 12 at the leading edge LE and trailing edge TE. Use of teeth with sufficiently small radius of curvature in transition from tip 111 to leading edge LE or trailing edge TE could result in structures depicted and shown in FIGS. 1 and 2.

Although web substrate 10 is disclosed in preferred embodiments as a two-layer web made from two precursor webs, it is not necessary for the web substrate 10 to be limited to two such layers. For example, a three-layer or more laminate made from three precursor webs, or a co-extruded web material having at least three layers disposed therein can be used as long as one of the precursor webs or layers can extend and push through openings in another layer to form protuberances. By way of example, web substrate 10 could comprise a top sheet, a bottom sheet, and a core having an activatable substrate disposed therebetween. In general, it is not necessary that adhesive or other bonding means be utilized to make a laminate suitable for use as web substrate 10.

The constituent layers of web substrate 10; that is, first precursor film 12 and second precursor film 14 and any additional layers, can be held in a face-to-face laminated relationship by virtue of the locking effect due to the formation of protuberances 16 that extend through openings 20 and first precursor film 12. In some embodiments, it may be desirable to use adhesive or thermal bonding or other bonding means depending upon the end use application of web substrate 10. For example, a web substrate 10 comprising bi-component polymeric materials can be bonded after formation of protuberances 16 to provide for layer-to-layer adhesion for greater peel strength. Additionally, it may be desirable to apply an adhesive to at least one portion of any of the precursor webs. For example, in some embodiments, adhesive chemical bonding, resin, powder bonding, or thermal bonding between representative layers can be selectively applied to certain regions or all of each of the precursor webs. For example, in the case of adhesive application, an adhesive can be applied in a continuous manner such as by slot coating or in a discontinuous manner such as by spraying, extruding, and the like. Discontinuous application of adhesive can be in the form of stripes, bands, droplets, and the like. Such adhesive application can be in an amorphous pattern, if so desired.

As would be known to one of skill in the art, depending upon the first precursor film 12 and the second precursor film 14 chosen and the dimensional parameters of rolls 102 including teeth 110, web substrate 10 of the present invention can exhibit a wide range of physical properties. The web substrate 10 can exhibit a range of textures subjectively experienced as ranging from softness to roughness, a bulkiness ranging from relatively low bulk to relatively high bulk, a tear strength ranging from low tear strength to high tear strength, elasticity ranging from non-elastic to at least 100% elastically extensible, a chemical resistance ranging from relatively low resistance to high resistance depending on the chemical considered, and many other variable parameters generally described as shielding performance, alkali resistance, opacity, wiping performance, water absorbtivity, oil absorbtivity, body fluid absorbtivity, moisture permeability, heat insulating properties, weather ability, high strength, high tear force, abrasion resistance, electrostatic controllability, drape, dye affinity, safety, and the like. In general, depending on the elongation properties of second precursor film 14, the dimensions of apparatus 100 can be varied to produce a web substrate 10 having a wide range of dimensions associated with protuberances 16, including the height H and spacing. Additionally, the protuberances 16 may easily be patterned into lines, filled forms, and selected regions of the laminate web by having the desired pattern displayed in the teeth 110 disposed upon roll 104.

Web substrate 10 may be used for a wide variety of applications including, but not limited to, sheets for various electric appliances such as capacitor separator paper, floppy disk packaging material, various industrial sheets such as tacky adhesive tape base material, various medicinal and sanitary sheets such as surgical gown covering material, cap, mask, diaper liners, diaper covers, feminine napkin covers, shopping bags, suit covers, pillow covers, agricultural sheets such as ground covers and erosion control devices, cooling and sunlight shielding cloth, lining, curtains, sheets for overall covering, light shielding materials, floor coverings, wrapping materials of pesticides, laboratory gowns and dust preventive clothes, various sheets for civil engineering buildings such as house wraps, drain materials, separation materials, overlays, roofing materials, wall interior materials, soundproof or vibration reducing sheet materials, curing sheet materials, automobile interior sheets such as floor mats and trunk mats, molded ceiling materials, headrests, lining cloths and separator sheets usable for alkaline batteries. Web substrate 10 may also be used for cleaning a surface. The surface may be a soft surface such as skin on the face or body or a hard surface such as a floor, counter, table, or desk. A body wash cloth, facial cleansing implement, pedicure pad, and other skin cleansing implements may utilize the web substrate 10. Hard surface cleaning implements include a scrubbing and cleansing strips, wipes, and mops are also desired. Further, web substrate 10 can be coated or treated with other lotions, medicaments, cleaning fluids, antibacterial solutions, emulsions, fragrances, surfactants, and the like. As would be known to one of skill in the art, second precursor film 14 can be provided with at least one fragrance that can be activated upon use of the web material 10. By way of example, a base fragrance can be extruded with the film comprising second precursor film 14 that is subsequently formed into web substrate 10, as discussed supra. Such a fragrance could be released into the surrounding environment on a continuous basis. Alternatively, a mixture of an encapsulated mixture containing a fragrance can be applied onto second precursor film 14. In a preferred embodiment, such a mixture would not release a fragrance until the appropriate sheer force was applied to the capsule. Such an appropriate sheer force can be applied by stretching the polymeric films that have been used as first precursor film 12 and second precursor film 14 to produce web substrate 10, as described herein.

Further, the placement of multiple layers of films having differing colors, such as co-extruded and/or laminated films, can be treated as discussed herein by providing the aforementioned layers with differing degrees of strains, thereby facilitating a change in opacity of each layer. Thus, in a web substrate 10, produced with a second precursor film 14 having a plurality of layers of differing colors or having different film characteristics, processing as described herein can provide layers that would normally be masked or muted to show through the final product to provide a web material having an appearance different than what would otherwise be available by conventional means. Alternatively, second precursor film 14 can be provided with layers having different strain rates so that the outer layers rupture or break, thereby completely exposing any inner layers. Any inner layers could be provided with differing colors or other actives; for example, fragrances, odor absorbing or neutralizing agents, liquid absorbing agents, and the like that would be now exposed to the surface through first precursor film 12.

In yet another alternative embodiment, second precursor film 14 can be provided with strain or sheer sensitive materials within the film structure so that when the precursor web is treated as disclosed herein, the induced strain or sheer can cause a visible or functional product change. By way of example, additives such as encapsulated dyes and inks can be used so that the encapsulation fails when they are ruptured to provide visible changes. Further, this process can be used to provide other functional items; for example, fragrances, odor neutralizing components, moisture control components, oxidizing agents, anti-oxidizing agents, and the like within second precursor film 14 and ultimately into web substrate 10. This can result in improved aesthetics and/or improved functionality for constructed film materials useful in products such as bags and wraps. Further, if the web substrate 10 of the current invention is formed into a container, such as a bag-like structure, as disclosed in U.S. Pat. No. 6,394,652, a fragrance can be applied to the web substrate 10 in a manner that facilitates activation upon the application of a force internal or external to the web substrate 10. For example, perfumed oils can be added or incorporated into an extruded film material applied to the surface of a film material or applied to a device that applies the perfumed oil to the film. In such a bag embodiment, a fragrance or odor neutralizing component provided in a microencapsulated substrate can be activated when the bag is filled, thereby releasing the fragrance or other actives when needed and minimizing release of the fragrance or other additive when not in use.

Another advantage of the process described to produce the webs of the present invention is that the webs can be produced in line with other web production equipment. Additionally, there may be other solid-state formation processes that can be used either prior or after the process of the present invention. For example, a web could be processed according to the present invention and then apertured with a stretching process, such as the one described in U.S. Pat. No. 5,658,639. Alternatively, material could be made into a composite through a variety of processes, such as the one described in U.S. Patent Publication No. 2003/028,165 A1. Further, the material can be process or ring rolled, for example, as described in U.S. Pat. No. 5,167,897 and then processed according to the present invention. The resulting web can thus exhibit the combined benefits of these multiple material modifications.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web material for a container, said web material comprising a first precursor web and second precursor web, said first precursor web comprising a polymeric film material, said web material having a first side comprising said first precursor web and at least one protuberance having a linear orientation defining a longitudinal axis disposed thereon, each of said protuberances comprising said second precursor web, wherein said protuberances are integral extensions of said second precursor web extending through said first precursor web, said web material further comprising a second side comprising said second precursor web, said web material forming a semi-enclosed container having an opening defined by a periphery, said opening defining an opening plane, said container being expandable in response to forces exerted by contents within said container to provide an increase in volume of said container such that said container accommodates the contents placed therein.

2. The web material of claim 1, wherein said container includes a closure means for sealing said opening to convert said semi-enclosed container to a substantially closed container.

3. The web material of claim 1, wherein said web material is a planar sheet of material.

4. The web material of claim 1, wherein said protuberances comprise a second region and said first precursor web comprises a first region, a portion of said first region extending in a first direction while the remainder of said first region extends in a second direction perpendicular to said first direction to intersect one another, said first region forming a boundary completely surrounding said second region.

5. The web material of claim 4, wherein said first region and said second region are visually distinct from one another.

6. The web material of claim 4, wherein said first region is substantially free of said protuberances.

7. The web material of claim 1, wherein said web material exhibits at least two significantly different stages of resistive force to an applied axial elongation along at least one axis when subjected to the applied axial elongation in a direction parallel to the axis in response to an externally applied force upon said web material.

8. The web material of claim 1, wherein said container is a bag.

9. The web material of claim 1, wherein said first precursor web has elongation properties less than said second precursor web.

* * * * *